United States Patent [19]

Solomons et al.

[11] 3,937,654

[45] Feb. 10, 1976

[54] PRODUCTION OF EDIBLE PROTEIN SUBSTANCES

[75] Inventors: Gerald L. Solomons, High Wycombe; Gerald W. Scammell, Chinnor, both of England

[73] Assignee: Ranks Hovis McDougall Limited, London, England

[22] Filed: July 25, 1975

[21] Appl. No.: 599,026

Related U.S. Application Data

[63] Continuation of Ser. No. 459,021, April 8, 1974, abandoned, which is a continuation of Ser. No. 140,303, May 4, 1971, abandoned.

[30] Foreign Application Priority Data

May 14, 1970 United Kingdom .............. 23452/70

June 24, 1970 United Kingdom .............. 30584/70

[52] U.S. Cl. ...................... 195/35; 195/79; 195/81; 195/112; 195/115; 426/48; 426/60

[51] Int. Cl.$^2$ ...................... C12B 1/08; C12D 13/06

[58] Field of Search .......... 195/31, 35, 81, 112, 79, 195/115, 76, 13; 426/48, 60

[56] References Cited

UNITED STATES PATENTS

| | | | |
|---|---|---|---|
| 2,450,055 | 9/1948 | Nord | 426/72 |
| 2,822,319 | 2/1958 | Monod | 195/115 |
| 3,151,038 | 2/1964 | Gray et al. | 195/32 |

FOREIGN PATENTS OR APPLICATIONS

| | | | |
|---|---|---|---|
| 1,085,994 | 10/1967 | United Kingdom | 195/28 R |

OTHER PUBLICATIONS

Vinson et al., "The Nutritive Value of Fusaria," Science, Vol. 101, No. 2624, pp. 388–389 (1945).

Chian et al., "Growth of Mixed Cultures on Mixed Substrates," Applied Microbiology, Sept. 1968, pp. 1337–1342.

Imholte et al., J. Pharm. Sci., Vol. 57, No. 1, pp. 97–100, (1968).

*Primary Examiner*—A. Louis Monacell
*Assistant Examiner*—Thomas G. Wiseman
*Attorney, Agent, or Firm*—Stevens, Davis, Miller & Mosher

[57] ABSTRACT

Process for the production of an edible protein-containing substance which comprises incubating and proliferating, under aerobic conditions, a non-toxic strain of the gensus Fusarium or a variant or mutant thereof, in a culture medium containing essential growth-promoting nutrient substances, of which carbon in the form of assimilable carbohydrate constitutes the limiting substrate in proliferation, and separating the proliferated organism comprising the edible protein-containing substance. Novel strains and variants of *Fusarium graminearum* are also disclosed.

25 Claims, No Drawings

PRODUCTION OF EDIBLE PROTEIN SUBSTANCES

This is a Continuation of application Ser. No. 459,021 filed Apr. 8, 1974, now abandoned, which in turn is a continuation of Ser. No. 140,303 filed May 4, 1971, now abandoned.

The present invention relates to a process for the production of edible protein-containing substances and has particular reference to the production of fungal protein by microbial action.

Our copending United Kingdom Application No. 53312/66, Ser. No. 1210356, relates to a process for the production of an edible protein-containing substance which comprises incubating and proliferating, under aerobic conditions, an organism which is a non-toxic strain of a microfungus of the class Fungi Imperfecti, in a culture medium containing essential growth-promoting nutrient substances, of which carbon in the form of assimilable carbohydrate constitutes the limiting substrate in proliferation, and separating from a assimilable carbohydrate exhausted medium the prolifereated organism which constitutes the edible protein-containing substance.

It is also an object of the present invention to provide fungal mycelium which possesses a high net protein utilisation value on rat assays of at least 70 based on the α-amino nitrogen. However, as indicated in one of the examples, it is possible to have a net protein utilization value of at least 65.

According to the present invention there is provided a process for the production of an edible protein-containing substance which comprises incubating and proliferating, under aerobic conditions, non-toxic strain of the genus Fusarium or a variant or mutant thereof, in a culture medium containing essential growth-promoting nutrient substances, of which carbon in the form of assimilable carbohydrate constitutes, the limiting substrate in proliferation, and separating the proliferated organism comprising the edible protein-containing substance.

The separated proliferated organism comprising the edible protein-containing substance may be incorporated into a foodstuff for human or animal consumption.

The substrate employed in the incubation stage may be of vegetable origin, for example starch, starch containing materials or products of their hydrolysis, sucrose, sucrose containing materials or hydrolysed sucrose i.e. invert sugar or mixtures thereof. Thus the substrate may comprise hydrolysed potato, molasses, glucose, hydrolysed bean starch or cassava. Alternatively substrate of animal origin comprising whey may be employed.

The non-toxic strain of Fusarium may be a strain of *Fusarium graminearum*.

The preferred non-toxic strain is our strain of *Fusarium graminearum* Schwabe, deposited with the Commonwealth Mycological Institute and assigned the number I.M.I. 145425 and variants and mutants thereof.

The following novel variants may also be employed:

I-7 deposited with the Commonwealth Mycological Institute and assigned the number I.M.I. 154209.

I-8 deposited with the Commonwealth Mycological Institute and assigned the number I.M.I. 154211.

I-9 deposited with the Commonwealth Mycological Institute and assigned the number I.M.I. 154212.

I-15 deposited with the Commonwealth Mycological Institute and assigned the number I.M.I. 154213.

I-16 deposited with the Commonwealth Mycological Institute and assigned the number I.M.I. 154210.

Our new strain of *Fusarium graminearum* Schwabe, I.M.I 145425, is non-pathogenic to wheat. It has the following morphological characteristics:

Media

Potato Sucrose Agar

Czapek-Dox (Modified) Agar (oxoid)

250 grams of potatoes washed and diced, placed in pressure cooker 15 lbs. square inch for 15 minutes. The decoction is then squeezed through two layers of muslin. 2% of Glucose & 2% of Agar are added to the turbid filtrate and the medium autoclaved and dispersed.

Growth conditions 25°C. several weeks

Rate of growth: 4.0 cm. in 3 days 3.0 cm. in 3 days

Character of growth: Floccose, spreading colonies with white aerial mycelium. Substratum on PSA greyish rose with patches of crimson to yellow. Tendency to be somewhat paler on CDA. Occasionally deep red pigment produced, particularly on ageing. After one to two weeks the aerial mycelium tends to become brown and collapse. The colony then becomes rather slimy as sporodochia are formed the colour being pink to brown on PSA and salmon pink on CDA. No exudate is formed and pigment formation tends to follow the mycelium colour.

Conidia: Microconidia not produced by this organism. Macroconidia produced from single lateral phialides or multibranched conidiophores with short phialides. In older cultures the conidiophores aggregate to form sporodochia, particularly on CDA. The conidia vary from falcate to curved fusoid dorsi-ventral, septation varying from 3 to 5, commonly 5 in younger cultures. Spore size varies from $25 - 50\mu \times 2.5\ \mu - 4.0\ \mu$. The foot cell is often pedicellate, particularly in the longer 5 septate spores. Swollen cells occur in the mycelium and occasionally chlamydospores occur intercalary, singly or in chains.

Following is a description by way of example of the preparation of variants (or isolates) of *Fusarium graminearum* Schwabe I.M.I. 145425 and their morphological characteristics.

Isolates obtained from continuous culture

*Fusarium graminearum* Schwabe I.M.I. 154209 to 154213 were selected from malt extract agar plates inoculated with broth from a fermenter growing *Fusarium graminearum* Schwabe 145245 on a glucose/salts medium at 30°C. under continuous culture conditions with carbon limitation at a dilution rate of 0.1 – 0.15 $hr^{-1}$. The fermenter was sampled at approximately 100 hour intervals to assess the population of variants and the isolates I.M.I. 154209 to 154213 were taken from the plates prepared from the 1100 hour sample. These isolates are representative of the major types of morphological variant produced during the fermentation. Under these conditions outlined in this example the variants begin to appear on plates from 800 hours onwards. They are continually produced from this time onward and the population slowly changes as regards the percentage of each type. The fermenter conditions are as follow:

| | Culture medium | % |
|---|---|---|
| Solution 1 | Glucose | 3.0 |
| | Ammonium sulphate | 0.25 |
| | Potassium di-hydrogen phosphate | 0.30 |
| | Magnesium sulphate | 0.025 |
| | Antifoam, polypropylene glycol 2000; sterilised at pH 3.0 for 30 mins. at 15 p.s.i.g. | 0.01 |
| Solution 2 | $MnSO_4\ 4H_2O$ | 0.0005 |
| | $FESO_4\ 7H_2O$ | 0.0005 |
| | $ZnSO_4\ 7H_2O$ | 0.0005 |
| | $CoCl_2\ 6H_2O$ | 0.0001 |
| | $CuSO_4\ 5H_2O$ | 0.0001 |
| | $Na_2MoO_4\ 2H_2O$ | 0.0001 |
| | Sterilised 15 mins. at 15 p.s.i.g. | |
| Solution 3 | Biotin | 0,10 or 20 μg/l |
| | Choline | 0,1 or 2 mg/l |
| | Methionine | 0 or 600 mg/l |
| | Sterilised separately by filtration | |

All solutions were added, as necessary, aseptically to the medium reservoir then fed to the 8.5 litre chemostat with the following growth conditions: Temperature 30°C., aeration 1vvm (i.e., 1 volume air/volume culture medium/minute); agitation 800 r.p.m., single 6-bladed disc turbine, 0.5D, in fully baffled fermenter. The fermenter pH was maintained at 5.0 by the automatic addition of sterile ammonia. Solution 3 as changed in composition at various times to determine $\mu$max with the various such as biotin alone or biotin plus choline. Growth rate 0.1 to 0.15 $hr^{-1}$.

The five isolates have the following morphological characteristics.

Media

Potato Sucrose Agar

Czapek Dox Agar (Oxoid)

250 grams of potatoes washed and diced, placed in pressure cooker 15 lbs. square inch for 15 minutes. The decoction is then squeezed through two layers of muslin. 2% of Glucose & 2% of Agar are added to the turbid filtrate and the medium autoclaved and dispersed.

Growth conditions: 25°C.

Character of growth

Isolate I-7

Colony morphology similar to parent A3/5 except colony diameter is smaller, 1.5 cm in three days at 30°C. on C.D.A. The floccose aerial mycelium varies in degree from colony to colony but is less than I-8. Older cultures have a brown discoloration to the mycelium. Reverse, yellow-brown to greyish-rose sectors with some pigment diffusing.

Isolate I-8

Very intense white floccose aerial mycelium. Colony diameter again less than parent A3/5, 2.0 cm in 3 days at 30°C. on C.D.A. Reverse salmon pink to greyish-rose segments.

Isolate I-9

Macroscopic appearance close to I-8 but reverse lighter, salmon to hyaline in colour.

Isolate I-15

Small restricted dome shape colonies. Mycelium short, tangled and with tendency to be convoluted. Many sporodochia-like structure formed giving pink appearance at point of inoculation of streak. Pink coloration at periphery. Colony diameter only 0.4cm at 3 days at 30°C. on C.D.A.

Isolate I-16

Isolate I-15 is very unstable and continually gives rise to I-16. This isolate has an appearance similar to I-7 although colonies tend to be slightly greater in diameter, 2.4cm. in 3 days and more even in appearance. I-16 is more stable than I-15.

Conidia

Isolate I-7

Abundant macroconidia produced in similar fashion to parent A3/5. Sporodochia formed in older cultures. Individual macroconidia similar to parent A3/5 in shape and size, 25–50$\mu$ × 3.0–5.0$\mu$. In older cultures many sporodochia are formed. Chlamydospores are also abundant in the mycelium of this isolate, intercalary and terminal. They are globose smooth 10–12$\mu$. Occasionally a single cell of a macroconidium forms a chlamydospore.

Isolate I-8

Fewer macroconidia than I-7 and those present mainly smaller and simpler, 1 to 3 septate, 25–35$\mu$ in length. Few sporodochia formed. Chlamydospores again abundant, intercalary, terminal, single and in chains.

Isolate I-9

Very similar to I-8 except more macroconidia, almost equivalent to I-7 in number.

Isolate I-15

Very few macroconidia, the sporodochia-type structures are in fact made up of packets of chlamydospores. There are also many chlamydospores present in the mycelium. The macroconidia are smaller than the parent, 30–35$\mu$ × 4$\mu$ with only 2 septa.

Isolate I-16

Very similar to I-7 with abundant macroconidia and chlamydospores. The macroconidia are typical, 30–45$\mu$ × 4$\mu$.

The temperature of incubation in the process of the invention is in general between 25° and 34°C., preferably around 30°C.

Inoculation resulting in commencement of the process is best carried out by a pregerminated seed stage comprising for example from 2 to 10% of inoculum, usually in the range 5 to 10%.

The pH of the substrate medium during incubation is preferably kept within a suitable range supporting maximum growth, for example, between 3.5 to 7.

The period of growth in batch culture under the above mentioned conditions is usually found to range from 20 to 48 hours. In both batch and continuous processes aeration and agitation should be carried out to provide a sufficient level of dissolved oxygen to overcome deficiency which can be a limiting growth factor.

As will be well understood by those skilled in the art sufficient quantities of essential growth nutrients such as nitrogen, sulphur, phosphorus and other trace elements are maintained in the substrate medium so that growth of the substance is limited only by the carbohydrate available to the fungus.

In addition to the nutrients stated above the presence of one or more vitamins such for example as biotin may be desirable to maintain maximum growth rate.

It is also desirable to add a non-toxic antifoaming agent to the substrate medium to control foaming during the fermentation.

The substance produced according to the present invention may be isolated in any suitable manner known in the art. Thus the resulting mycelium may be recovered by separation, washing, filtration and drying. In this connection, however, it has been found that if the moisture content of the substance is reduced below a critical level of about 50% (w/w) by filtration under pressure the subsequent drying methods employed are not subjected to such stringent temperature limitations which is an important factor in the economic processing of these materials. The method of drying must not cause damage to the nutritional value of the mycelium and may be drying in a current of air at 75°C. or freeze drying.

The fungal mycelium produced by the process of the present invention shows very good water binding capacity and may be useful as a thickening and gelling agent. Not being an isolate, it retains its vitamins as well as other nutritionally available materials such as lipids and some carbohydrates. Fungal mycelium has satisfactory baking characteristics which are of value in protein enriched breads, breakfast foods and food snacks. The fungal mycelium, because of its filamentous structure, can be baked, fried or puffed and presented to many communities as a food comparable in appearance and acceptability with conventional foods which they are accustomed to eating.

Following is a description by No., of example of methods of carrying the invention into effect. Examples 1–4 are of batch culture.

EXAMPLE 1

10 Litres of the following culture medium were prepared and sterilised as described in a stirred fermenter vessel.

| | |
|---|---|
| Cane molasses to provide | 6% w/v sugar |
| Ammonium sulphate | 1.2% |
| $NaH_2PO_4$ | 0.25% |
| Sterilised 30 minutes | 15 psig |
| $CaCO_3$ | 0.5% w/v |
| Sterilised 3 hours | 15 psig |

The medium components were added aseptically and attemperated to 30°C. An inoculum equivalent to 5–10% by volume of the culture medium and grown either on a glucose/corn steep liquor medium or other suitable materials in shake flasks was inoculated with a spore suspension of the organism comprising our strain of *Fusarium graminearum* Schwabe I.M.I. 145425, and grown for 18–24 hours at 30°C. on a rotary shaker, and added aseptically to the fermenter.

The fermenter incubated at 30°C. was then stirred at 800 rpm with a 6-bladed disc turbine (0.5D) in a full baffled vessel and 1 VVM of sterile air passed through. After 35 hours, the grown mycelium was removed from the fermenter, centrifuged, washed with water and dried in a warm air band drier, air temperature 75°C.

The dried product had the following composition:

| | | |
|---|---|---|
| Total Nitrogen | 8.0% | |
| Ash | 5.3% | |
| Lipid | 2.7% | |
| NPUop. | 52 | based on Total Nitrogen |

where NPU op. is Net Protein Utilization (operative).

EXAMPLE 2

10 Litres of the following culture medium were prepared and sterilised as described, in a 14 litre New Brunswick, Microferm, fermenter.

| | | | Final % |
|---|---|---|---|
| Solution 1 | Glucose | pH 3.0 | 3.0 |
| Solution 2 | Ammonium sulphate | | 0.7 |
| Solution 3 | Potassium di-hydrogen phosphate | pH 5.0 | 1.0 |
| Solution 4 | $FeSO_4\ 7H_2O$ | pH 2.5 | 0.001 |
| | $MnSO_4\ 4H_2O$ | | 0.0005 |
| | $CuSO_4\ 5H_2O$ | | 0.0001 |
| | $MgSO_4\ 7H_2O$ | | 0.025 |
| Solution 5 | $Na_2MoO_4\ 2H_2O$ | | 0.0001 |
| | $CoCl_2\ 6H_2O$ | | 0.0001 |
| | $CaCl_2\ 2\ H_2O$ | | 0.0015 |
| Solution 6 | NaOH | | 0.1 |

All the above solutions were sterilised by heat for 15 minutes at 15 psig.

Solution 7 Vitamins and/or amino acids as described below sterilised by filtration.

The solutions were added aseptically to the vessel.

An inoculum was grown and added as in Example 1 except that the final concentration in the fermenter was adjusted so as to provide 0.5 gm/1 dry wt. of mycelium.

The conditions of growth were temperature 30°C; aeration 1VVM, stirrer speed was adjusted to maintain a level of dissolved oxygen above 25% of the saturation value in the culture medium, measured by a New Brunswick Inc. DO probe. Sterile anti-foam, polypropylene glycol 2000, was added as required to suppress foam and pH was maintained between 6.0 – 6.3 by the addition of sterile potassium hydroxide solution.

| | | Growth rates ($hr.^{-1}$) |
|---|---|---|
| (i) | Omitting solution 7 (Minimal medium) | very slow |
| (ii) | Solution 7 such that the final concentration of Biotin in the culture medium was 30 $\mu$g/l | 0.2 |
| (iii) | Solution 7 such that the final concentration of Biotin in the culture medium was 50 $\mu$g/l; Choline chloride 30 mg/l and Methionine 300 mg/l | 0.25 |

EXAMPLE 3

Medium and conditions were as in Example 2, but the glucose was replaced with maltose.

| | | |
|---|---|---|
| (i) | Solution 7 as Example 2 (ii) | 0.18 |
| (ii) | Solution 7 as Example 2 (iii) | 0.21 |

EXAMPLE 4

100 Litres of the following culture medium were prepared and sterilised as described in a 130 l. stainless steel fermenter.

| | % final concentration |
|---|---|
| Glucose | 4.0 |
| Corn steep liquor (50% Total Solids) | 0.8 |
| Ammonium sulphate | 0.2 |

-continued

| | % final concentration |
|---|---|
| Potassium di-hydrogen phosphate | 0.2 |
| MG $SO_4$ $7H_2O$ | 0.025 |
| Zn $SO_4$ $7H_2O$ | 0.0005 |
| Fe $SO_4$ $7H_2O$ | 0.0005 |
| Mn $SO_4$ $4H_2O$ | 0.0001 |

The medium was sterilised at pH 3.0 at 15 psig for 30 minutes and on cooling to 30°C. adjusted to pH 5.0 by the sterile addition of ammonia.

Biotin sterilised by filtration to give 40 $\mu$g/l final concentration, was added aseptically.

The vessel was inoculated with 10 litres of culture grown in a sparged vessel, for 18 hours, at 30°C., on a medium containing: Glucose 2%; tryptone (oxoid) 0.4%; yeast extract (oxoid) 0.1%; ammonium sulphate 0.15%; potassium di-hydrogen phosphate 1%; sodium hydroxide 0.1%; magnesium sulphate 0.025%; ferrous sulphate 0.001%; zinc sulphate 0.001%; manganese sulphate 0.0005%; copper sulphate 0.001%; anti-foam, polypropylene glycol 2000 0.05% and sterilised for 45 minutes at 15 psig, inoculated with a spore suspension of our organism *Fusarium graminearum* Schwabe I.M.I. 145425.

The conditions for growth were temperature 30°C., aeration adjusted to provide dissolved oxygen concentrations above 10% of the saturation value for the culture broth. Sterile anti-foam, polypropylene glycol 2000, was added to suppress foaming, and the pH was maintained at 5.0 by means of sterile ammonia additions. Samples of the mycelium taken over the period of growth contained, on a dry weight basis: Total Nitrogen 8.0 – 8.6%; $\alpha$-Amino nitrogen 6.4 – 6.6%. The initial growth rate in this complex medium derived from both the batched culture medium and inoculum was approximately 0.3 $hr.^{-1}$.

The following Examples 5 and 6 are of continuous culture.

EXAMPLE 5

Culture medium of the following composition was prepared:

| Solution 1 | Final % |
|---|---|
| Glucose | 3.0 |
| Ammonium sulphate | 0.25 |
| Potassium di-hydrogen phosphate | 0.3 |
| Magnesium sulphate | 0.025 |
| Anti-foam, polypropylene glycol 2000 | 0.01 |
| Sterilised at pH 3.0 for 30 minutes at 15 psig | |

-continued

| Solution 2 | Final % |
|---|---|
| $MnSO_4$ $4H_2O$ | 0.0005 |
| $FeSO_4$ $7H_2O$ | 0.0005 |
| $ZnSO_4$ $7H_2O$ | 0.0005 |
| $CoCl_2$ $6H_2O$ | 0.0001 |
| $CuSO_4$ $5H_2O$ | 0.0001 |
| $Na_2MoO_4$ $2H_2O$ | 0.0001 |
| Sterilised 15 minutes at 15 psig | |

Solution 3

Vitamins and/or amino acid as described below sterilised by filtration.

All solutions were added as necessary, aseptically. In 8.5 litre chemostat the conditions of growth were as follows:

Temperature 30°C; aeration 1VVM; agitation 800 rpm single 6-bladed disc turbine 0.5 D in fully baffled vessel. Organism, our strain of *Fusarium graminearum* Schwabe I.M.I. 145425. The pH maintained at 5.0 by automatic addition of sterile ammonia.

| | | Mycelium | | | | | |
|---|---|---|---|---|---|---|---|
| | | $\mu$Max. $hr.^{-1}$ | Yield factor | TN% | AN% | NPU based on TN | NPU based on AN |
| (i) | Solution 3 such that the final concentrate of Biotin in the culture medium was 20 $\mu$g/l | 0.17–0.19 | 0.5 | 7.2 to 7.9 | 6.3 to 6.8 | 54 | 65 |
| (ii) | Solution 3 such that the final concentration of Biotin in the culture medium was 20 $\mu$g/l and of methionine was 600 mg/l | 0.20–0.21 | 0.5 | 7.7 to 8.6 | 6.1 to 6.5 | 59 | 78 |

EXAMPLE 6

Culture medium of the following composition was prepared:

| | % |
|---|---|
| Bean starch ($\alpha$-amylase treated) | 3.0 carbohydrate |
| Corn steep liquor | 1.33 |
| Ammonium sulphate | 0.25 |
| Potassium di-hydrogen phosphate | 0.15 |
| Magnesium sulphate | 0.025 |
| Antifoam polypropylene glycol 2000 (v/w) | 0.025 |
| Sterilised pH 4.0 for 30 minutes at 15 p.s.i.g. | |

The medium was fed to the 8.5 litre chemostat under the same conditions as in Example 5 except that the pH was varied between 3.5 and 6.0 and growth rate throughout 0.1 $hr^{-1}$. The following result was obtained:

| | TN% | AN% | NPU based on TN | NPU based on AN |
|---|---|---|---|---|
| Product grown at pH 4.0 | 7.8 | 6.6 | 54 | 67 |
| Product grown at pH 5.0 | 8.6 | 7.1 | 57 | 71 |
| Product grown at pH 6.0 | 7.7 | 5.9 | 61 | 80 |

Example 6*b*

The culture medium and conditions were as in Example 6 except that the pH was held at 5.0 throughout the run and the temperature was varied between 26° and 34°C. The optimum temperature was found to be 30°–32°C.

Examples 7 to 12 describe the fermentation of five variants or isolates of *Fusarium graminearum* Schwabe I.M.I. 145425.

EXAMPLE 7

Duplicate shake flasks of 1-litre capacity were prepared containing 200 mls. of the following medium:

| | | Final concentration % |
|---|---|---|
| Solution 1 | Glucose (sterilised separately pH 3.0 10 p.s.i./10 min.) | 3.0 |
| Solution 2 | Ammonium sulphate | 0.565 |
| | Potassium Dihydrogen Phosphate | 1.0 |
| | $MgSO_4$:$7H_2O$ | 0.025 |
| | $FeSO_4$:$(NH_4)_2SO_4$:$6H_2O$ | 0.0005 |
| | $MnSO_4$:$4H_2O$ | 0.0005 |
| | $CuSO_4$:$5H_2O$ | 0.0001 |
| | $CoCl_2$:$6H_2O$ | 0.0001 |
| | $CaCl_2$:$2H_2O$ | 0.0015 |
| | $Na_2MoO_4$ $2H_2O$ | 0.00001 |
| | NaOH | 0.2 |
| | Salts sterilised at 15 p.s.i.g./15 min. Final pH 6.0 | |

Solution 3 Vitamins as described below were sterilised by filtration

The solutions were added aseptically to give a final volume of 200 ml. then the flasks were inoculated with washed spores of our strain of *Fusarium graminearum* I-7 I.M.I. 154209 to give a concentration of 8 × $10^3$/ml.

The conditions of growth were temperature 30°C., 140 r.p.m. on orbital shaker with 2 inch throw.

At hourly intervals the growth was measured by measuring the Optical Density of a sample at 600 mμ. From the results obtained the following growth rates were established.

| | | Growth rate $h^{-1}$ |
|---|---|---|
| (i) | Solution 3 omitted (minimal medium) | very slow |
| (ii) | Solution 3 such that the final concentration of Biotin in the culture medium was 50μg/l | 0.22 |
| (iii) | Solution 3 such that the final concentration of Biotin in the culture medium was 50μg/l and Choline chloride 50 mg/l. | 0.27 |

EXAMPLE 8

The procedure of Example 7 was repeated but the strain I-7 was replaced by our strain of *Fusarium graminearum* Schwabe I-8. The following growth rates were established:

| | | Growth rate $h^{-1}$ |
|---|---|---|
| (i) | As 7(i) | very slow |
| (ii) | As 7(ii) | 0.22 |
| (iii) | As 7(iii) | 0.27 |

EXAMPLE 9

The procedure of Example 7 was repeated but the strain I-7 was replaced by our strain of *Fusarium graminearum* Schwabe I-9. The following growth rates were established:

| | | Growth rate $h^{-1}$ |
|---|---|---|
| (i) | As 7(i) | very slow |
| (ii) | As 7(ii) | 0.21 |
| (iii) | As 7(iii) | 0.27 |

EXAMPLE 10

The procedure of Example 7 was repeated but the strain I-7 was replaced by our strain of *Fusarium graminearum* Schwabe I-15. The following growth rates were established:

| | | Growth rate $h^{-1}$ |
|---|---|---|
| (i) | As 7(i) | very slow |
| (ii) | As 7(ii) | 0.21 |
| (iii) | As 7(iii) | 0.27 |

EXAMPLE 11

The procedure of Example 7 was repeated but the strain I-7 was replaced by our strain of *Fusarium graminearum* Schwabe I-16. The following growth rates were established:

| | | Growth rate $h^{-1}$ |
|---|---|---|
| (i) | As 7(i) | very slow |
| (ii) | As 7(ii) | 0.21 |
| (iii) | As 7(iii) | 0.27 |

EXAMPLE 12

The procedure of Example 7 was repeated but the strain I-7 was replaced by the parent strain *Fusarium graminearum* Schwabe I.M.I. 145425. The following growth rates were established:

| | | Growth rate $h^{-1}$ |
|---|---|---|
| (i) | As 7(i) | very slow |
| (ii) | As 7(ii) | 0.22 |
| (iii) | As 7(iii) | 0.27 |

Examples 13 and 14 describe fermentation using strains of Fusaria other than Fusarium graminearum.

EXAMPLE 13

A spore suspension of *Fusarium solani* strain A7-16 (I.M.I. 154217) was inoculated into a seed fermenter of 80 litre volume containing a glucose, corn steep liquor medium. After growing up the seed fermenter to 10 to 20 gms. per litre, it was split in two, 40 litres to each 400 litre vessel. The seed was inoculated into a medium of the following composition:

| | % |
|---|---|
| Starch | 6.0 |
| $KH_2PO_4$ | 0.20 |
| $(NH_4)_2SO_4$ | 0.25 |
| Corn Steep Liquor (50% Total Solids) | 0.50 |

pH was 5.5 maintained by addition of sterile ammonia; Temperature 30°C. Pressure 30 p.s.i.g. Air rate 1.0 v.v.m. The revolutions of the stirrer were increased steadily from 92 to 184 r.p.m. to maintain dissolved oxygen in the vessel. The agitator consisted of two turbines 0.4D. When the carbohydrate had been utilised the grown mycelium was removed from the fermenter, filtered, washed with water, centrifuged, and dried in a warm air band drier at 75°C. The dried product had the following composition:

| | |
|---|---|
| Total nitrogen | 9.1% |
| Ash | 8.3% |

When fed to rats this material gave an NPUop of 41 based on Total Nitrogen.

EXAMPLE 14

*Fusarium oxysporum* strain A9-23 (I.M.I. 154214) was grown exactly as in the previous example except the starch was replaced by cane molasses at a concentration that produced 6.0% sugars.

The dried product had the following composition:

| | |
|---|---|
| Total nitrogen | 9.9% |
| Ash | 10.8% |
| NPUop | 47.0 based on Total Nitrogen |

Methods of analysis for Total Nitrogen (TN) Automatic Kjeldahl digestor (Technicon). A. Ferrari, Ann. N.Y. Sci. 87, 792 (1960).

Amino nitrogen (AN) TNBS (modified). M. A. Pinnegar, Technicon Symposium 1965, p. 80.

We claim:

1. A process for the production of an edible protein-containing substance which comprises incubating and proliferating, under aerobic conditions, a non-toxic strain of the genus Fusarium or a variant or mutant thereof in a culture medium containing all essential growth-promoting nutrient substances, of which carbon in the form of assimilable carbohydrate constitutes the limiting substrate in proliferation, and separating the proliferated organism comprising the edible protein-containing substance possessing a high net protein utilization value of at least 70 based on the $\alpha$-amino nitrogen.

2. A process as claimed in claim 1 wherein the separated proliferated organism comprising the edible protein-containing substance is incorporated into a foodstuff for human or animal consumption.

3. A process as claimed in claim 1 wherein the substrate comprises starch, starch containing materials, or products of their hydrolysis, sucrose, sucrose containing materials, hydrolysed sucrose, or mixtures thereof.

4. A process as claimed in claim 1 wherein the substrate comprises hydrolysed potato, molasses, glucose, maltose, hydrolysed bean starch or whey.

5. A process as claimed in claim 1 wherein the temperature of incubation is between 25° and 34°C.

6. A process as claimed in claim 1 wherein the pH of the substrate medium during incubation is between 3.5 and 7.

7. A process as claimed in claim 1 wherein the process is carried out in continuous culture.

8. A process as claimed in claim 1 wherein the process is carried out in batch culture.

9. A process as claimed in claim 1 wherein at least one vitamin is present in the culture medium.

10. A process as claimed in claim 1 wherein the non-toxic strain of Fusarium is a strain of *Fusarium graminearum*.

11. A process as claimed in claim 9 wherein biotin is present.

12. A process for the production of an edible protein-containing substance which comprises incubating and proliferating, under aerobic conditions a non-toxic strain of the genus Fusarium or a variant or mutant thereof in a culture medium containing biotin and all essential growth-promoting nutrient substances, of which carbon in the form of assimilable carbohydrate constitutes the limiting substrate in proliferation, and separating the proliferated organism comprising the edible protein-containing substance possessing a high net protein utilization value of at least 70 based on the $\alpha$-amino nitrogen.

13. A process as claimed in claim 1 wherein the non-toxic strain of the genus Fusarium is selected from the species consisting of *Fusarium graminearum*, *Fusarium solani* and *Fusarium oxysporum* or a variant or mutant thereof.

14. A process for the production of an edible protein-containing substance which comprises incubating and proliferating, under aerobic conditions, a non-toxic strain of a variant I7, I-8, I-9, I-15 or I-16 of our parent strain of *Fusarium graminearum* Schwabe IMI 145425 deposited with the Commonwealth Mycological Institute and respectively assigned the numbers IMI 154209, IMI 154211, IMI 154212, IMI 154213 or IMI 154210 in a culture medium containing essential growth-promoting nutrient substances, of which carbon in the form of assimilable carbohydrate constitutes the limiting substrate in proliferation, and separating the proliferated organism comprising the edible protein-containing substance.

15. A process for the production of an edible protein-containing substance which comprises incubating and proliferating, under aerobic conditions, a non-toxic strain of *Fusarium graminearum* Schwabe deposited with the Commonwealth Mycological Institute and assigned the number IMI 145425 or a variant or mutant thereof in a culture medium containing all essential growth-promoting nutrient substances, of which carbon in the form of assimilable carbohydrate constitutes the limiting substrate in proliferation, and separating the proliferated organism comprising the edible protein-containing substance, possessing a high net protein utilization value of at least 70 based on the $\alpha$-amino nitrogen.

16. A process for the production of an edible protein-containing substance which comprises incubating and proliferating, under aerobic conditions, a non-toxic strain of *Fusarium solani* or *Fusarium oxysporum* or a variant or mutant thereof in a culture medium containing all essential growth-promoting nutrient substances, of which carbon in the form of assimilable carbohydrate constitutes the limiting substrate in proliferation, and separating the proliferated organism comprising the edible protein-containing substance, possessing a high net protein utilization value of at least 70 based on the α-amino nitrogen.

17. A method for the preparation of variants of *Fusarium graminearum* Schwabe IMI 145425 which comprises growing the parent strain IMI 145425 under continuous culture conditions with carbon limitation in a fermentation.

18. A method as claimed in claim 17 which comprises growing the parent strain IMI 145425 on a glucose based medium at 25° to 30°C under continuous culture conditions at a dilution rate of 0.10 to 0.15 hrs. $^{-1}$ with carbon limitation in a fermentation for 1100 hours.

19. A method as claimed in claim 18 wherein the resulting proliferated variants are isolated by dilution plating.

20. A method for cultivating a strain of *Fusarium graminearum* Schwabe IMI 145425 or a mutant or variant thereof wherein the strain is present in a culture medium containing or being supplied with all nutrients or additives necessary for the sustenance and multiplication of the strain, the medium having a pH between 3.5 and 7 at a temperature of between 25° and 34°C and wherein the carbon in the form of assimilable carbohydrate constitutes the limiting substrate in proliferation.

21. A process for the production of an edible protein-containing substance which comprises incubating and proliferating, under aerobic conditions, a non-toxic strain of the genus Fusarium or a variant or mutant thereof in a culture medium containing all essential growth-promoting nutrient substances, of which carbon in the form of assimilable carbohydrate constitutes the limiting substrate in proliferation, and separating the proliferated organism comprising the edible protein-containing substance possessing a high net protein utilization value of at least 65 based on the α-amino nitrogen.

22. A process for the production of an edible protein-containing substance which comprises incubating and proliferating, under aerobic conditions, a non-toxic strain of the genus Fusarium or a variant or mutant thereof in a culture medium containing biotin and all essential growth-promoting nutrient substances, of which carbon in the form of assimilable carbohydrate constitutes the limiting substrate in proliferation, and separating the proliferated organism comprising the edible protein-containing substance possessing a high net protein utilization value of at least 65 based on the α-amino nitrogen.

23. A process for the production of an edible protein-containing substance which comprises incubating and proliferating, under aerobic conditions, a non-toxic strain of *Fusarium graminearum* Schwabe deposited with the Commonwealth Mycological Institute and assigned the number IMI 145425 or a variant or mutant thereof in a culture medium containing all essential growth-promoting nutrient substances, of which carbon in the form of assimilable carbohydrate constitutes the limiting substrate in proliferation, and separating the proliferated organism comprising the edible protein-containing substance possessing a high net protein utilization value of at least 65 based on the α-amino nitrogen.

24. A process for the production of an edible protein-containing substance which comprises incubating and proliferating, under aerobic conditions, non-toxic strain of *Fusarium graminearum* Schwabe deposited with the Commonwealth Mycological Institute and assigned the number IMI 145425 or a variant or mutant thereof in a culture medium containing all essential growth-promoting nutrient substances, of which carbon in the form of assimilable carbohydrate constitutes the limiting substrate in proliferating, and separating the proliferated organism comprising the edible protein-containing substance.

25. A process for the production of an edible protein-containing substance which comprises incubating and proliferating, under aerobic conditions, a non-toxic strain of *Fusarium solani* or *Fusarium oxysporum* or a variant or mutant thereof in a culture medium containing all essential growth-promoting nutrient substances, of which carbon in the form of assimilable carbohydrate constitutes the limiting substrate in proliferation, and separating the proliferated organism comprising the edible protein-containing substance.

* * * * *